(12) United States Patent
Thind et al.

(10) Patent No.: US 10,984,909 B2
(45) Date of Patent: Apr. 20, 2021

(54) GAS CYLINDER MONITORING SYSTEM

(71) Applicant: LINDE AKTIENGESELLSCHAFT, Munich (DE)

(72) Inventors: Mandip Thind, Southall (GB); Rigoberto Perez De Alejo Fortun, Guildford (GB); Brian Jacobsen, Horsham (GB)

(73) Assignee: LINDE AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 16/099,504

(22) PCT Filed: May 8, 2017

(86) PCT No.: PCT/EP2017/060949
§ 371 (c)(1),
(2) Date: Nov. 7, 2018

(87) PCT Pub. No.: WO2017/194481
PCT Pub. Date: Nov. 16, 2017

(65) Prior Publication Data
US 2019/0107253 A1  Apr. 11, 2019

(30) Foreign Application Priority Data
May 13, 2016 (GB) ...................... 1608487

(51) Int. Cl.
*G16H 40/67* (2018.01)
*G06Q 10/08* (2012.01)
(Continued)

(52) U.S. Cl.
CPC ........ *G16H 40/67* (2018.01); *A61M 16/0051* (2013.01); *F17C 13/02* (2013.01);
(Continued)

(58) Field of Classification Search
None
See application file for complete search history.

(56) References Cited

U.S. PATENT DOCUMENTS 5,953,682 A     9/1999   McCarrick et al.
6,150,921 A *  11/2000   Werb .................... G01S 13/878
                                                        340/10.1
(Continued)

OTHER PUBLICATIONS

International Search Report for PCT/EP2017/060940, dated Aug. 25, 2017, Authorized Officer: Alexander Gardiner, 3 pages.

*Primary Examiner* — Curtis J King
(74) *Attorney, Agent, or Firm* — Millen White Zelano & Branigan, PC; Brion P. Heaney

(57) ABSTRACT

A gas cylinder monitoring system is disclosed having a gas cylinder for receiving and distributing gas contained therein, a first monitoring system associated with the gas cylinder operable to monitor data associated with the gas cylinder and having a transmitter operable to broadcast the data at a controlled time and/or time interval in a discrete advertisement package, and a second monitoring system associated with one or more locations in which the first monitoring system may reside and having a receiver operable in a first mode to receive the advertisement package broadcast from the first monitoring system when the second monitoring system is within range of the first monitoring system.

31 Claims, 3 Drawing Sheets

(51) Int. Cl.
*A61M 16/00* (2006.01)
*F17C 13/02* (2006.01)

(52) U.S. Cl.
CPC ......... *G06Q 10/08* (2013.01); *G06Q 10/0832* (2013.01); *A61M 2205/18* (2013.01); *A61M 2205/3584* (2013.01); *F17C 2250/032* (2013.01); *F17C 2250/034* (2013.01); *F17C 2250/036* (2013.01); *F17C 2270/02* (2013.01); *F17C 2270/0745* (2013.01); *G06Q 10/087* (2013.01)

(56) References Cited

U.S. PATENT DOCUMENTS

| | | | | |
|---|---|---|---|---|
| 6,763,843 | B1* | 7/2004 | Dickerson, Jr. | F17C 13/045 137/1 |
| 7,479,884 | B1* | 1/2009 | Fullerton | G01S 13/003 340/572.7 |
| 2002/0020444 | A1* | 2/2002 | Dickerson, Jr. | F17C 13/045 137/112 |
| 2003/0195644 | A1* | 10/2003 | Borders | A47C 31/008 700/90 |
| 2004/0194980 | A1* | 10/2004 | McSheffrey, Jr. | G08B 25/10 169/75 |
| 2005/0056090 | A1* | 3/2005 | McSheffrey, Jr. | A62C 37/50 73/291 |
| 2006/0007039 | A1* | 1/2006 | Duvall | G01S 5/0027 342/357.55 |
| 2008/0079606 | A1* | 4/2008 | Spare | F17C 13/025 340/870.16 |
| 2008/0084306 | A1* | 4/2008 | Durtschi | G06Q 10/087 340/572.1 |
| 2008/0150739 | A1* | 6/2008 | Gamard | F17C 13/003 340/626 |
| 2008/0221808 | A1* | 9/2008 | Dix | F17C 13/025 702/36 |
| 2008/0251074 | A1* | 10/2008 | Sand | A61M 16/10 128/204.18 |
| 2008/0272896 | A1* | 11/2008 | Adamczyk | G08B 13/1427 340/426.1 |
| 2008/0303717 | A1* | 12/2008 | Durban | G01S 1/44 342/371 |
| 2009/0140867 | A1* | 6/2009 | Yin | F17C 13/003 340/626 |
| 2009/0146793 | A1* | 6/2009 | Fullerton | G06K 19/0723 340/10.4 |
| 2010/0192695 | A1* | 8/2010 | McSheffrey, Jr. | A62C 37/50 73/753 |
| 2011/0128129 | A1* | 6/2011 | Graczyk | G06K 17/0022 340/10.33 |
| 2011/0140850 | A1* | 6/2011 | Wassel | F17C 13/021 340/8.1 |
| 2012/0030368 | A1* | 2/2012 | John | H04N 21/23109 709/231 |
| 2012/0188076 | A1* | 7/2012 | McSheffrey | A62C 13/76 340/539.17 |
| 2013/0006886 | A1* | 1/2013 | Estes | G06Q 10/0833 705/332 |
| 2014/0266625 | A1* | 9/2014 | Merlin | G06K 7/10366 340/10.1 |
| 2016/0098673 | A1* | 4/2016 | Lavra | G06Q 10/087 235/385 |
| 2016/0104100 | A1* | 4/2016 | Ratermann | G06Q 10/087 235/385 |
| 2017/0061090 | A1* | 3/2017 | Itoh | H04W 4/029 |
| 2017/0074707 | A1* | 3/2017 | Mathison | G01F 22/00 |
| 2017/0307141 | A1* | 10/2017 | Essey | F17C 13/028 |
| 2018/0044159 | A1* | 2/2018 | Crouse | G06N 3/08 |

* cited by examiner

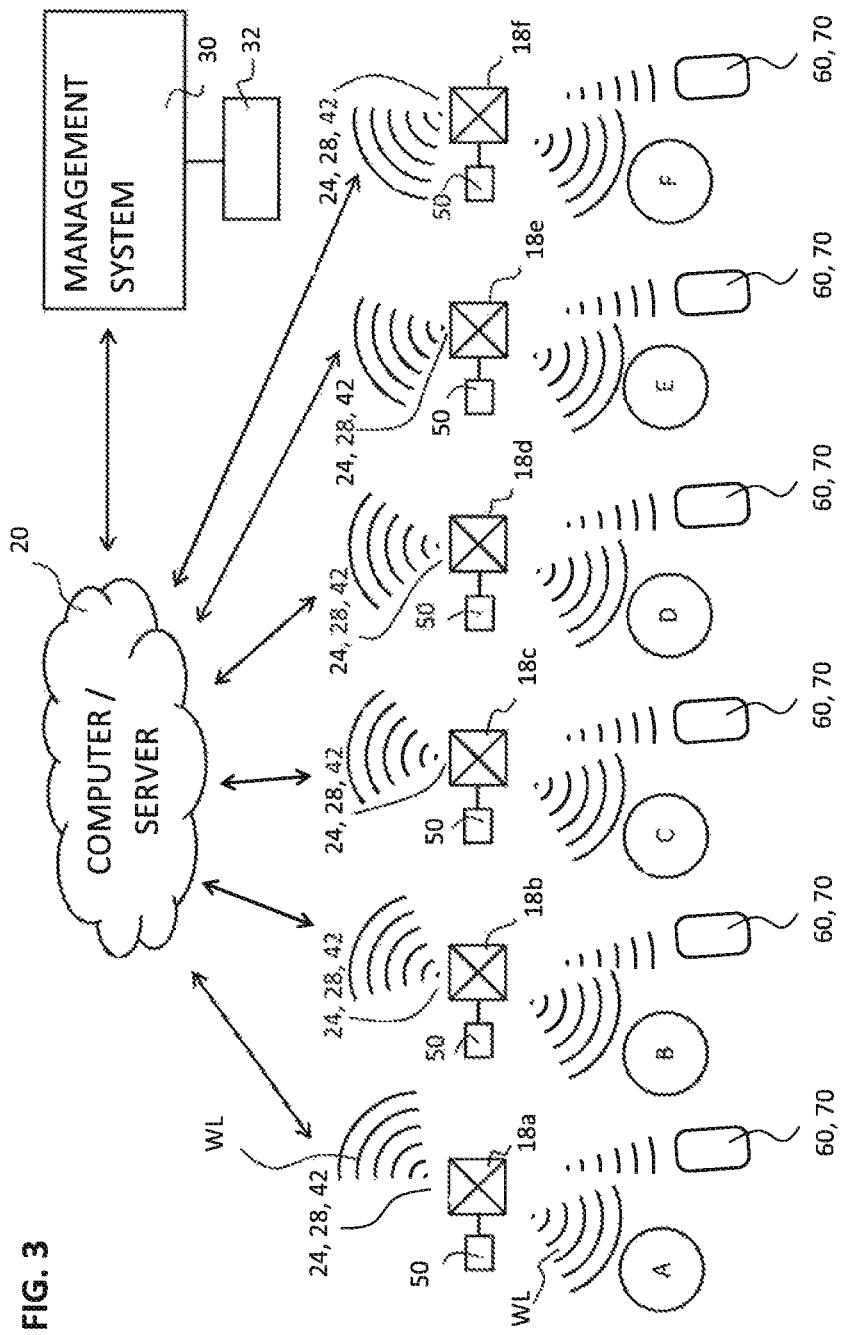

GAS CYLINDER MONITORING SYSTEM

CROSS-REFERENCE TO RELATED APPLICATIONS

This application claims priority under 35 USC § 119 to International Patent Application No. PCT/EP2017/060949, filed on May 8, 2017 which claims priority from Great Britain Patent Application GB 16 084 87.3, filed on May 13, 2016.

BACKGROUND OF THE INVENTION

The present invention relates to a gas cylinder monitoring system, in particular to a gas cylinder monitoring system using gas cylinders for supplying clinical gasses such as, for example, oxygen, argon, nitrous oxide, xenon, nitric oxide, helium and mixtures thereof to patients, and for supplying industrial gases such as oxygen, nitrogen and argon and mixtures thereof.

It is known to supply gas cylinders into a process including filling, transporting, storing and using before having the cylinders returned to the supplier for re-filling and then re-circulation within the process. The tracking of cylinders and the management of gas supply whilst at locations within the process is problematic as it is sometimes difficult to monitor the location of the cylinders and the data associated with the cylinder, for example, and importantly, the time remaining before the cylinder runs out of gas.

It is also known to supply cylinder systems with gauges displaying the pressure of gas remaining, but human intervention is required in order to retrieve the information and some users may find it difficult to interpret the information supplied and may make incorrect determinations of important data such as the total time of gas supply remaining. Still further, it is very difficult to locate cylinder systems which may be past their use-by date or which may be obsolete or inappropriate for a particular location.

In an attempt to overcome the above problems, known gas cylinders are provided with an electronic monitoring system which is attached to the gas cylinder to monitor the data associated with the cylinder as well as enable the location of the gas cylinder to be determined. The monitoring system can wirelessly transmit the data to a remote computer which includes a management system to analyse the data and determine the cylinder location. Such a monitoring system ensures the cylinders are in the correct state for the location in which they reside.

Since the cylinders are frequently being moved from location to location, such as from a storage station to a hospital ward, the monitoring systems themselves are powered by batteries. One problem with battery powered monitoring systems is the energy intensive nature of the wireless transmissions which result in the batteries draining quickly and can eventually lead to inoperation of the monitoring system and therefore not knowing the status and/or the location of the gas cylinders.

SUMMARY OF THE INVENTION

An object of the present invention is to provide a less energy intensive monitoring system for a gas cylinder which enables the status and location of the gas cylinder to be determined.

Thus, according to the present invention there is provided a gas cylinder monitoring system comprising a gas cylinder for receiving and distributing gas contained therein, a first monitoring system associated with the gas cylinder operable to monitor data associated with the gas cylinder and having a transmitter operable to broadcast the data at a controlled time and/or time interval in a discrete advertisement package, and a second monitoring system associated with one or more locations in which the first monitoring system may reside and having a receiver operable in a first mode to receive the advertisement package broadcast from the first monitoring system when the second monitoring system is within range of the first monitoring system.

By broadcasting the advertisement package at a controlled time and/or time interval, less data is sent and therefore less energy is consumed compared to systems where data is sent with no control or continuously.

Further, by broadcasting the data in a discrete advertisement package, typically in less than 50 milliseconds, energy consumption is further reduced.

Turning to data transmission in general, it is known to transmit data between devices using different wireless standards. One such standard is the Bluetooth® wireless technology standard. More specifically, one device is said to be in discoverable mode, i.e. it is continuously sending data, which connects to a second device when the two devices are in range of each other. Once the two devices are connected or paired, data can be transmitted between the two. It should be understood that when the second monitoring system is operable in a first mode to receive the advertisement package from the first monitoring system, the first and second monitoring systems do not become connected or paired as is the case with devices using conventional wireless transmission standards such as Bluetooth®. Instead, the advertisement package is transmitted as a discrete package from the first monitoring system and received by the second monitoring system without the need for pairing or connecting. This results in less energy being consumed when compared to devices which connect or pair with each other to enable data transmission.

Preferably the advertisement package includes data associated with the cylinder and/or the patient and/or the environment. The data itself falls into two categories, one category which is fixed data that does not vary with the cylinder, patient or environment, and a second variable data category. Examples of fixed data include cylinder identification number, cylinder size, firmware version, expiry date and cylinder type. Examples of variable data include cylinder pressure, cylinder operating mode, battery life, tamper state, gas supply time remaining, environmental temperature, gas usage, gas content, time since filling, rate of gas usage, internal cylinder gas pressure, internal cylinder gas temperature, usage data, transportation data, and gas remaining. By broadcasting data which is variable, the advertisement package can be considered as dynamic in the sense that the package contents will change according to the operation of the cylinder and/or the patient and/or the environment, which contrasts with know systems where the data is fixed.

Analysis of the data by a processor of the first monitoring system determines the time and/or time interval at which the advertisement package is broadcast. For example, as the time remaining before the cylinder empties approaches a critical lower threshold, or the rate of gas consumption increases, the advertisement package is sent more frequently. In contrast, if the gas cylinder is in storage, and the variable data does not change, then the advertisement package is sent less frequently. By varying the time and/or time interval at which the advertisement packages is sent, less energy is consumed, which is made possible by being able to monitor and broadcast the variable data. Analysis of data by the first monitoring system can also control an output of the gas cylinder such as disabling an alarm if silence is required such as on a ward, or controlling gas flow to titrate a patient depending on oxygen saturation in the patient's blood, closing the gas valve if a hazard is detected, or if the cylinder expiry date has lapsed.

The advertisement package can also be broadcast at time intervals that depend on the operational mode of the gas cylinder, for example a deep sleep mode, a connected mode, a standby mode, a gas delivery mode, or a fault mode. As an example, the time interval is less than 2 minutes when the gas cylinder is in a critical mode such as gas delivery mode, typically between 30 seconds and 1 minute, and broadcast of the data is greater than 30 minutes when the gas cylinder is in a less critical mode, for example in a storage station or in a sleep mode. For non-critical modes other than storage or filling for example, the broadcast time is in the region of 2 to 6 minutes.

The advertisement package can also be broadcast at a time corresponding to pre-defined events, for example, if the remaining gas supply time reaches a lower threshold, if the gas cylinder enters a fault mode, a gas delivery mode or a connected mode, or if the gas cylinder enters or leaves a gas filling station.

In one embodiment, the advertisement package is immediately broadcast if movement of the first monitoring system is detected by an optional motion sensor. Therefore an alternative and additional sensor for monitoring the gas cylinder is provided to trigger immediate broadcast of the advertisement package.

Preferably the second monitoring system comprises a plurality of hub stations at known locations and the system includes a processor operable to identify the known location of the hub stations receiving data from the first monitoring system to determine the location of the first monitoring system. By positioning the hub stations at, and within different locations in broadcasting range of the first monitoring system, it is possible to locate the first monitoring system and therefore the gas cylinder. If more than one hub station is receiving data from the first monitoring system, the signal strength between the first and individual hub stations of the second monitoring system or triangulation between multiple hub stations can be used to determine the location of the first monitoring system. The advantage of using triangulation between hub stations is that the exact location of the first monitoring system can be determined which is important as the signal strength is not a reliable indicator of hub station proximity. For example, if an obstacle such as a wall is situated between the first monitoring system and the closest hub station, the signal strength is likely to be stronger between the first monitoring system and a different hub station that is further away due to the wall reducing the signal strength, and therefore the first monitoring would be incorrectly located by the hub station that is further away. This can be critical if the closest hub station is an Intensive Care Unit (ICU) whereas the detected closest hub station based on signal strength is a storage station or some other location where the status of the gas cylinder to which the first monitoring is associated is less important.

In one embodiment, instead of the first monitoring system processing data and determining the time and/or time interval at which advertisement packages are broadcast, the analysis of the data can be undertaken by a processor of the second monitoring system or of a further device with instructions based on the data then being transmitted to the first monitoring system. The instructions can configuring the advertisement package, varying the time and/or time interval at which data is broadcast from the first monitoring system, or controlling an output of the gas cylinder.

In addition to broadcasting the advertisement package at a time and/or time interval dependent on the data associated with the gas cylinder, the package can be broadcast at a time and/or time interval dependent on the location of the gas cylinder which is determined by association with one or more of the hub stations. It is also possible to infer the location of the gas cylinder from the data within the advertisement package being broadcast, for example, when being filled, or delivering gas, and therefore whilst being able to determine the location of the first monitoring system from the hub station is advantageous, it is not essential to enable controlled broadcasting of the advertisement package.

The transmitter and receivers associated with the first and second monitoring systems can use wireless technology such as Wi-Fi or Bluetooth. Preferably, data transmissions between the first and second monitoring systems use Bluetooth, most preferably low energy Bluetooth (BLE), and data transmissions between the second monitoring system and a computer or a cloud or a further device use Wi-Fi. This is advantageous as the use of Bluetooth transmission and reception with the first monitoring system further reduces energy consumption and preserves battery life of the first monitoring system, whereas the second monitoring system is connected to a mains power supply and therefore less concerned with power consumption.

Whilst the normal operating mode of the system is the first mode where the first and second monitoring systems do not connect or pair, this being the mode of operation for over 95% of the time, the receiver is further operable in a second mode to connect the second monitoring system to the first monitoring system to enable data transfer therebetween.

BRIEF DESCRIPTION OF THE DRAWINGS

The present invention will now be described by way of example only with reference to the accompanying drawings, in which:

FIG. 3 is a detailed view of one portion of the system shown in FIG. 2.

DETAILED DESCRIPTION OF THE INVENTION

Figure 1:
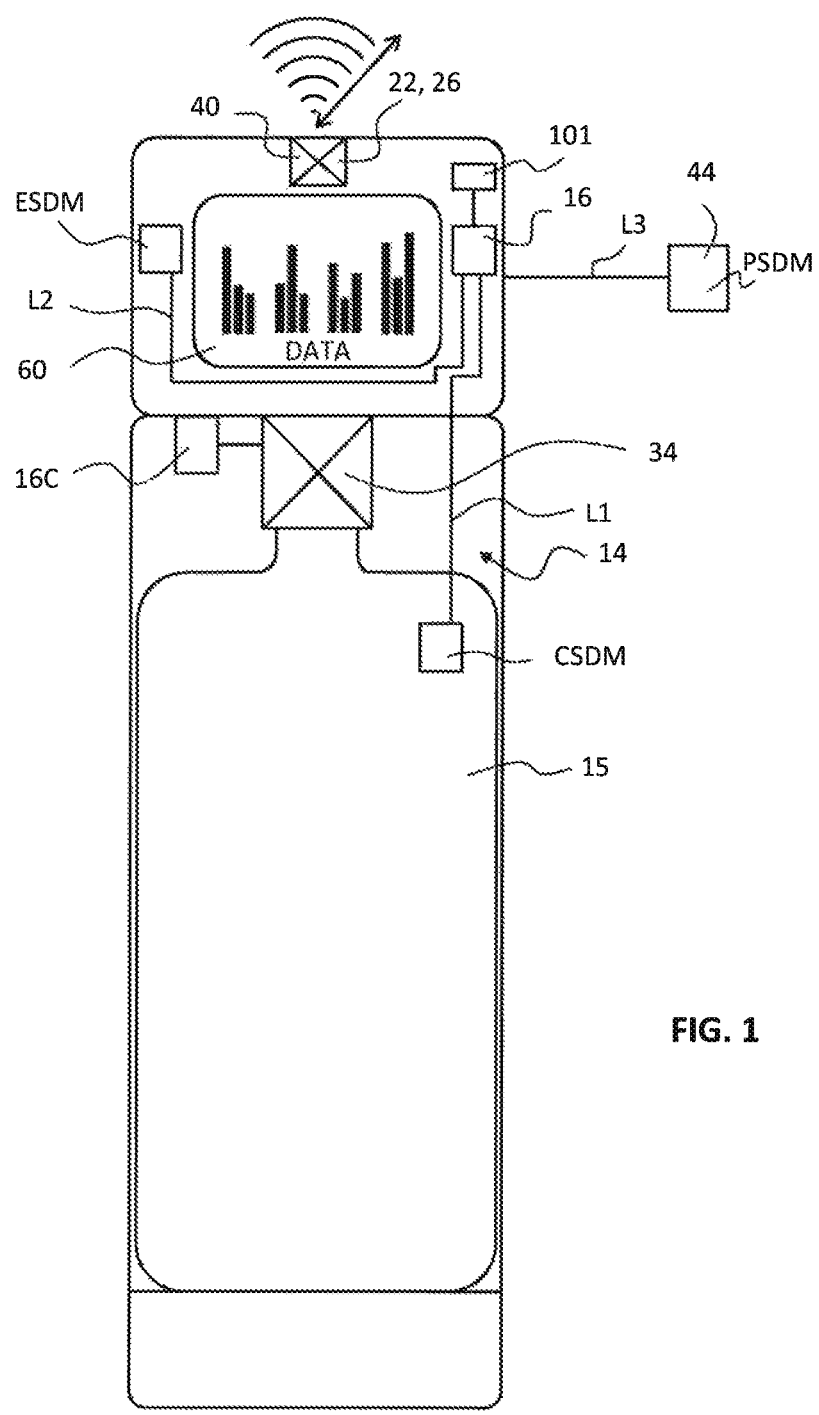
FIG. 1 is an overview of the system according to a first aspect of the present invention.
Figure 2:
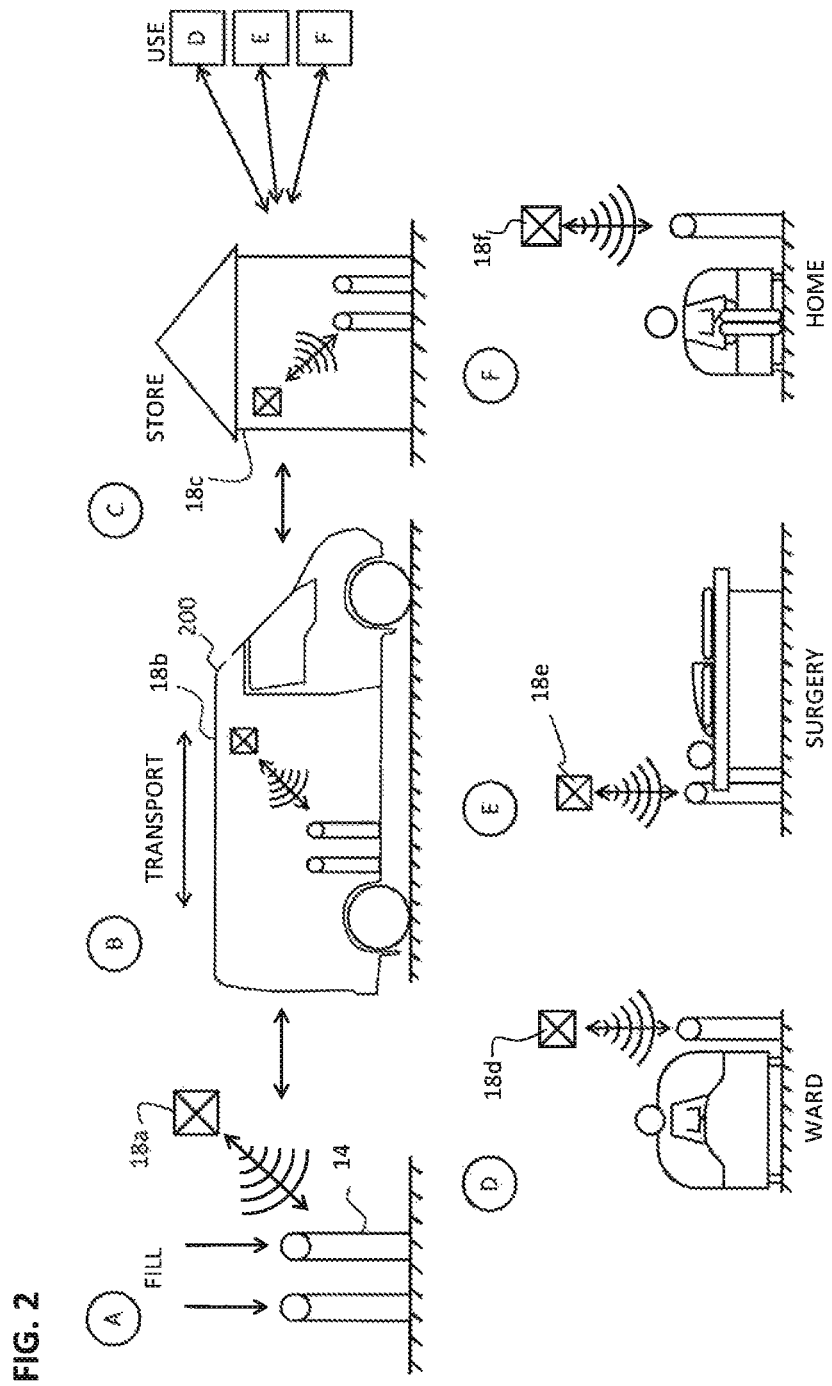
FIG. 2 is a general view of a cylinder in accordance with a second aspect of the present invention.

Referring now to the drawings in general but particularly to FIG. 1, it will be appreciated that a gas cylinder system 14 may be located in any one of a number of locations during its lifecycle and that it is often difficult simply to locate a cylinder that is known to be in the supply chain. The typical supply chain includes a number of locations including but not limited to a filling station (A), a transportation vehicle (B), a storage facility (C) and any one of a number of use locations such as those shown at D to F. Such use locations may include a hospital ward (D), surgery, (E) or home (F) as shown in FIG. 2.

The gas cylinder system 14 comprises a gas cylinder 15 and a first monitoring system 16 for monitoring cylinder specific data associated with the gas cylinder 15. The first monitoring system 16 is powered by a battery (not shown) as it is not practical to connect to a mains power supply as the gas cylinder system 14 is frequently moved from location to location, and within locations, for example within a hospital.

The first monitoring system 16 is provided with a low energy Bluetooth (BLE) transmitter 22 for broadcasting data in the form of an advertisement package (AP). The first monitoring system 16 may also be provided with a receiver 26 for receiving data or command signals from a second monitoring system 18 or further device. Each of these further devices is discussed in detail below. The first monitoring system 16 has an internal processor 23 which includes software to instruct the broadcasting of the advertisement package (AP) at a time interval and/or time which is dependent on the data being monitored.

Example contents of the advertisement package are shown in Table 1. It will be appreciated that the data in the advertisement package can be selected according to data considered important to the management of the gas supply, and includes fixed data and variable data.

TABLE 1

Example Advertisement Package

| Offset byte | Advertisement package | New Value (default) |
|---|---|---|
| 0 | Size of the Package | 0x19 |
| 1 | Flag BT standard | 0xFF |
| 2 | Indigo main ID | 0xFF |
| 3 | Indigo product ID | 0xFF |
| 4 | System Status | 0: Not connectable<br>1: Connectable |
| 5 | MCU all OK | Status of port pin (P1, 2) |
| 6 | Reserve Space | 1 |
| 7 | Operating mode<br>a) Modes not allowed in the version, so the value must not be received.<br>b) Mode is only allowed but not connectable<br>c) 3x button does not connect. Advertisement not connectable | 1: Deep sleep (mode a)<br>2: Connected (mode a)<br>3: Standby (sleep)<br>4: Gas delivery (mode b)<br>5: Fault (mode a)<br>6: Fill plant (mode c) |
| 8 | Tamper state (used since last filling) | 0: Not used<br>1: Used |
| 9-12 | History size | (9 - LSB, 12 - MSB) |
| 13-16 | PIC firmware version | 13 - major version<br>14- minor version<br>15 - release number<br>16-build number |
| 17-20 | BLE firmware version | 17- major version<br>18 - minor version<br>19 - release number<br>20 - build number |
| 21-22 | Cylinder pressure (cbar) | (21- LSB, 22- MSB) |
| 23-24 | Cylinder size (ml) | (23- LSB, 24- MSB) |

In FIGS. 2 and 3, one or more of the locations A to F are each provided with a second monitoring system in the form of hub stations 18a-f which each include a receiver 19a-f operable in a first mode to receive the advertisement package (AP) from the first monitoring system 16 without the first and second monitoring systems becoming connected or paired. Each of the hub stations 18a-f is in a known location and in contrast to the first monitoring system 16 which is battery powered, are connected to a mains power supply as there is no requirement for the hub stations 18a-f to move. Typically the hub stations 18a-f will be fixed to the wall in locations A, C, D, E and F, and in a convenient location in a transportation vehicle B.

Preferably, and where appropriate, for example in a location covering a large area such as a hospital, the locations are each provided with a plurality of hub stations such as the hospital ward (D) and the surgery (E). to ensure that at least one of the hub stations is able to receive data from the first monitoring system 16 within that location. Preferably, the second monitoring systems 18a-f are each operable to monitor at least the location of any cylinder system 14 provided with a first monitoring system 16 but they may be operable as described below to monitor more data and/or initiate commands/transmit data received from the first monitoring system 16 to a further device. The further device may be any one or more of a cloud based server or computer system 20, a further device 60 or a human interface system 70, each of which is described in more detail below. The further device 60 and/or human interface system 70 may be provided with a software application to facilitate human interaction including display of information and modification or control through human input.

Referring now more particularly to FIG. 1, the cylinder system 14 may also be provided with a cylinder specific data monitor (CSDM) for monitoring cylinder specific data such as, cylinder identification, gas supply time remaining, expiry date, cylinder type, cylinder location, environmental temperature, gas usage, time since filling, rate of gas usage, internal cylinder gas pressure, internal cylinder gas temperature, usage data, transportation data, battery life and gas remaining.

The gas cylinder 15 may also include an environment specific data monitor (ESDM) for monitoring environment specific data and/or a patient specific data monitor (PSDM) for monitoring patient specific data. The environment specific data may include any one or more of location, smoke, temperature, movement or vibration, whilst the patient specific data may include any one or more of oxygen saturation, patient identity, patient type, blood pressure, heart rate, breathing and gas usage.

Each of the monitors is operably connected via lines L1-L3 to the first monitoring system 16 for transmitting the data thereto. The cylinder system 14 may also include a global positioning system (GPS) and transmitter (GPS), a wireless transmitter (WT) or any such similar devices for broadcasting its location, as shown generally at 40.

The cylinder system 14 further includes a controllable outlet valve 34 for controlling the gas output from the cylinder 15, and the first monitoring system 16 includes a controller 16c operably linked to the outlet valve 34, wherein the valve 34 is controllable to alter or prevent the flow of gas from the cylinder 15 dependent upon commands received. Such commands are sent by the first monitoring system 16 which is monitoring the status of the gas cylinder 15. In one arrangement, the first monitoring system 16 may also be programmed to respond to one or more automatic valve closure commands upon receipt of an adverse situation signal generated by detection of any one or more of: smoke, adverse vibration, adverse movement, adverse temperature, excessive or non-programmed gas usage, excessive or unexpected gas pressure, gas dispensing in the absence of receipt of patient specific data passage of an expiry date or unexpected or non-programmed location of the cylinder system 14.

In an alternative embodiment, commands can be sent to the first monitoring system 16 from the second monitoring system 18, the further device 60 or the human interface 70. In this case, the first monitoring system 16 may also be programmed to respond to one or more automatic valve closure commands upon receipt of an adverse situation signal generated by detection of the absence of a command signal from the second monitoring system 18, the further device 60 or the human interface module 70.

The system may also include an automatic check and restart function for periodically checking received data after valve closure due to detection of an adverse situation signal and re-starting gas flow in the absence of receipt of a further adverse situation signal. The system may include an automatic check and restart function includes an intelligent restart function for allowing gas to be delivered in accordance with a pre-determined control strategy. These functions may be provided in the first monitoring system 16, the second monitoring system 18 or a further device such as a server or computer 20 as discussed below.

The first monitoring system 16 may include an operable mode in which it is fully operational and a sleep mode in which it is not fully operable but is able to be placed back into the operable mode upon detection of cylinder activity such as the valve being opened or on receipt of a signal from the second monitoring system 18 to cause the first monitoring system 16 to adopt the operable mode (OM) or the sleep mode (SM) as and when required. However, it will be appreciated such a signal may be sent from any other suitably functional device. Such suitable other devices include a human interface module 70 for providing information or warnings to a user or accepting cylinder operational command inputs from a user. Preferably, the human interface module 70 has multiple modes of operation and the first monitoring system 16 is operable to alter the mode of operation of the interface module 70 dependent upon an inputted signal from the second monitoring system 18. Such an imputed signal may comprise a location signal which, upon receipt by the first monitoring system causes the triggering of a change of state of one or other or both of the valve position and/or the status of the human interface module 70. The valve position may be altered such as to prevent or allow or restrict or control gas delivery when the cylinder is in a particular location or absent from a location with a second monitoring system. The human interface may be altered such as to: enable or disable audio alarms; mute such alarms; enable or disable visual alarms; reduce light output from such alarms. Any audio or visual alarms or displays may be provided separately to other portions of the interface 70 and may comprise discrete alarms or displays positioned at convenient locations on the cylinder system 14 or in close proximity thereto. The human interface module 70 may be operable to change or cancel any one or more of: audio output, visual output, operational command output, user access capability, user interface capability or operational capability. The human interface module 70 may also be operable to receive patient specific data and for displaying the same to a member of hospital staff, the patient or another person. The system 10 may also include a memory 101 for retrievably storing any one or more of patient specific data, cylinder specific data and environment specific data. This memory may be accessible by the human interface 70 such as to allow hospital staff to view patient specific data such as to make treatment decisions based thereon. Such an arrangement is of particular use when the memory 101 is incorporated in association with the cylinder system 14 such that it moves with the cylinder. This will allow hospital staff to quickly and easily read the patient specific data of an incoming or new patient and integrate that data into any patient management or any patient treatment programme. The memory may also be operably linked to the first monitoring system 16 such as to allow it to be accessible by the second monitoring system 18.

The second monitoring system 18 may also be operable to transmit any one or more of patient specific data, cylinder specific data or environment specific data to a further device 60, the human interface 70 or the computer system 20 for subsequent analysis thereon by any one of a number of members of staff who have access to the further device or the human interface 70.

The further device 60 mentioned above may be mounted on the cylinder itself or may be a freestanding computer 62 having a display, a hand-held computer device, a mobile telephone or any such similar device. Such devices are easily integrated into the system 10 and their use would allow data such as patient specific data to be more easily shared between those who need it. Such sharing of data will, inevitably, improve patient care.

Communication between any of the devices 16,18,20,60, 70 may be by means of wired connections W or wireless connections WL. The further device 60 and/or human interface system 70 may be provided with a software application to facilitate human interaction including display of information and modification or control through human input.

Referring now more particularly to FIG. 3, the system may further include a computer system 20 for receiving any one or more of the patient specific data, cylinder specific data and/or environment specific data. The computer 20 may be a mainframe computer in a hospital or a cloud based server. Either arrangement of computer 20 may be operably connected to a management system 30 for allowing management of the cylinder system 14 or the system as and when desired. Such a management system 30 may further include an input device such as a keyboard 32 or screen or may be linked to a further device 60 or human interface module 70. Typical management activities may include: controlling certain types of cylinders such that they are not able to dispense gas in certain locations or when outside of certain locations; restricting or stopping the supply of gas from cylinders during certain times; emergency shut-down of cylinders in the event of fire or other dangerous situations; initiating audio or visual alarms on cylinders; disabling audio or visual alarms on cylinders in sensitive environments or during quiet periods; communicating with hospital staff or patients through the human interface or alarms; providing cylinder location information to staff; ordering replacement cylinders in advance of gas expiry; disablement of cylinders if past their expiry date etc.

It will be appreciated that the second monitoring system 18a-f is important to some aspects of the present invention as it acts as the communicator between devices. In particular, it allows for data from the gas cylinder (via the first monitoring system with which it is associated), patient and environment monitoring systems to be communicated to the computer 20 and/or any one of a number of other devices and to allow commands, instructions, information and communications to be passed to the gas cylinders 15. The second monitoring system 18a-f may also be used to allow for communication between cylinders 15 and for the passage of user inputted or systema generated information between cylinders 15.

It will also be appreciated that any one or more or all of the computer 20, management system 30, memory 101, further device 60 or human interface 70 may be provided on or in close association with the actual cylinder system 14 so as to be movable therewith. Such an arrangement would give hospital staff immediate access to data and to controlling the supply of gas to the patient. In addition, the management system 30 may be operable to monitor patient specific data such as heart rate and/or oxygen saturation and amend the delivery of oxygen to the patient dependent upon predefined or specified control requirements. These control requirements may include any one or more of:

a) Inputting max and/or min oxygen saturation levels to be maintained
b) Monitoring oxygen saturation of the patient
c) Adjusting oxygen delivery depending upon received data on actual oxygen saturation
d) Adjusting the oxygen delivery in accordance with a pre-defined control algorithm and/or
e) Adjusting the oxygen deliver manually.

The system operates as follows.

The first monitoring system 16 broadcasts an advertisement package (AP) in a first mode at a give time interval according to its location and operating status.

The location of the first monitoring system 16 (and hence the gas cylinder) is determined by identifying which of the hub stations 18*a-f* (whose location is known) is receiving data from the first monitoring system 16 which is broadcasting advertisement packages (AP) in the first mode. If the advertisement package (AP) broadcast by the first monitoring system 16 is received by more than one hub station 18*a-f*, then the location of the first monitoring system 16 is determined by triangulating between the hub stations.

The status of the gas cylinder and/or patient data and/or environmental data is determined by analysis of the data within the advertisement package (AP), In Table 1, and as an example, the advertisement package (AP) shows offset byte 7 has a new value of 6 to indicate the gas cylinder is being filled, and the internal processor 23 instructs the transmitter 22 to broadcast no further advertisement packages until the status and/or location of the gas cylinder changes.

In this embodiment, the internal processor 23 of the first monitoring system 16 includes software to instruct the broadcasting of the advertisement package (AP) at a time interval and/or time which is dependent on the data being monitored, i.e. there is no requirement to broadcast the advertisement package (AP) from the first monitoring system to the second monitoring system 18 or a further device such as the computer system for the purpose of determining the time and/or time interval at which the advertisement package (AP) should be broadcast.

The software within the first monitoring system 16 can be configured such that the advertisement package (AP) is broadcast when the gas cylinder arrives in the filling station to identify the gas content of the cylinder, and again when the cylinder leaves the filling station to confirm the gas cylinder has been filled, and further that no broadcasts are made during filling.

After filling, a cylinder system 14 is usually transported in some manner by means of, for example, a delivery truck 200 which may also be fitted with a second monitoring system in the form of a hub station 18*b*. It will be appreciated that in the case of the truck 200, only one hub station 18*b* is required as the broadcasting range of the Bluetooth transmitter 22 of the first monitoring system 16 is sufficient to cover all locations within the truck 200. The hub station 18*b* may send signals to the first monitoring system 16 of the cylinder system 14 so as to ensure gas may not be dispensed during transit and/or to ensure audio alarms are set to maximum volume and may also be used to place the cylinder system 14 into a sleep mode such as to manage the power demand of the cylinder. Environment specific data may be used to control the cylinder valve and/or alarms in the event of an adverse environmental event such as detection of smoke, unexpected temperature variation or adverse vibration. In the case where the gas cylinder system is being transported using the truck 200, or for example in an ambulance (not shown), the second monitoring system 18 may communicate it's location by means of GPS transmission, which in turn identifies the location of the gas cylinder system 14 which is broadcasting data and identifiable to the second monitoring system, Knowing the location of the gas cylinders and the data associated with the gas cylinder enables the hospital to check that ordered gas cylinders are in transit and to advise staff what quantity of cylinders, gas type and cylinder type are being transported The software within the first monitoring system 16 or alternatively within the computer system 20 or with any further device in communication with the first monitoring system 16, can be configured such that the advertisement package (AP) is broadcast when the gas cylinder 15 is unloaded or unloaded from the truck 200 to confirm contents, and further that no or limited broadcasts are made during transportation. The location of the gas cylinder system 14 is identified in the same way as described above, except that the location of the hub station is determined by GPS.

Upon delivery to the store location C, the second monitoring system 18*c* will identify the gas cylinder system 14 in the same way as described in relation to the filling station. Again, the second monitoring system 18 may be used to manage any aspect of the cylinder system 14 mentioned herein but, in particular, it may be used to manage the power by placing the cylinders into sleep mode and may prevent gas being delivered by activating an auto-close mode on the cylinder valve 34. Again, environment specific data may be used to control the cylinder valve and/or alarms in the event of an adverse environmental event such as detection of smoke, unexpected temperature variation, adverse vibration etc.

The software within the first monitoring system 16 or alternatively within the computer system 20 or with any further device in communication with the first monitoring system, can be configured such that the advertisement package (AP) is broadcast when the gas cylinder enters or leaves the store location and that no or less frequent broadcasts are made whilst in storage. The location of the gas cylinder system is identified in the same way as described above in relation to the filling station. Typically, the advertisement package (AP) will be broadcast approximately every 30 minutes when the gas cylinder is in storage.

The cylinder system 14 may remain in the store C for some time or may then be onwardly transferred to locations in which gas is expected to be dispensed, such as those shown by way of example as locations D to F. In such locations it will be expected that the cylinders 15 will be required to deliver gas and, consequently, the control over the cylinder valve 34 is amended accordingly so as to allow such delivery. This control may be modified on a time basis so as to prevent delivery of gas during periods where gas would not be expected to be delivered and/or to prevent gas being delivered in the absence of patient specific data. In the example of location D, the cylinder system 14 is present on a hospital ward D and communicates with the hub station 18*d* so as to transfer cylinder specific information and/or patient specific data and/or environment specific data to the computer 20, a further device 60 or a human interface module 70, all of which have been discussed above. As described above, it is likely that in a hospital ward, more than one hub station will be required to ensure that there is always at least one hub station within broadcasting range of the first monitoring system 16.

It will be appreciated that when the gas cylinders are in locations D, E, or F, the time interval at which data is broadcast will be reduced because it is important to have regular updates as to the status of the gas cylinder and other data, in particular, the remaining gas supply time. When the gas cylinder 15 is being used to deliver gas, the first monitoring system 16 detects that the cylinder valve 34 is not only open but also delivering gas and therefore broadcasts the advertisement package at a given time interval, for example every 60 seconds, with typical broadcast times in these locations in the order of 30 seconds to 2 minutes. If the first monitoring system detects that gas is no longer being delivered, but the valve remains open, the time interval of broadcast increases to 5 minutes for example. If the first monitoring system detects that no gas has been delivered for a period of time, then the time interval will again increase until either gas starts to be delivered again, or some other status change of the cylinder or environment necessitates an immediate or more frequent broadcast.

The software can also be configured to immediately broadcast data when critical gas cylinder data reaches a certain threshold, for example, when the remaining gas supply time is low. The software can be further configured to increase the frequency of broadcasts (reducing the time interval between broadcasts) during particular events such as gas delivery, and further still to reduce the time interval between broadcasts as critical levels of data are approached, for example if the gas supply is running low, or if the battery level on the first monitoring system is close to rendering the first monitoring system inoperative which in itself needs to be avoided.

When the cylinder system 14 is at location D, it may be desirable to reduce the volume of any alarms during the night or at any other time, and it may also be desirable to ensure that cylinder specific data such as gas remaining is elevated in importance so as to ensure the continuity of supply in the event of heavy or unexpected use. In particular, patient specific data may be broadcast so as to inform staff of patient parameters upon which they may make clinical decisions. The transfer of patient specific data may also include stored patient specific data as stored in memory 101. Further information such as gas demand and gas flow may be broadcast so as to allow for the creation of an alarm or control signal in the event that the delivery does not match the demand or the patient is not responding to the gas delivery in the manner that would be expected. Such alarms would allow early investigation and amendment of treatment or modification of gas delivery or investigation and solving of any as delivery problems. Such problems may include the patient lying on the gas delivery supply or the supply being disconnected from the patient. Environment specific data may be used to close the cylinder valve 34 upon detection of smoke or any other adverse environment specific data. Smoke may be detected as a result of the patient having a cigarette, which may have significant safety implications if the gas being delivered is oxygen. Environment specific data may be used to amend the volume of any alarms or alter the control of the cylinder in any other way.

It will be appreciated that the management system 30 may be provided on the cylinder system 14 itself such as to provide a control system 10 immediately available to the medical staff without resorting to a further device. It will also be appreciated that the cylinder system 14 may include a human interface module 70 provided.

Use in surgery (location E) may require the audio alarms to be disabled or amended so as not to interfere with other alarms and the system 10 may be used to cause patient specific data to be transmitted to the computer 20 or sharing with other members of staff outside of the operating theatre or to further device 60 or a human interface module 70 for sharing in another way. During surgery, time intervals between data broadcasting may be smaller when compared to the time intervals on the ward (location D), for example every 30 seconds.

Use at home (location F) may require the human interface 70 to be caused to display simple instructions to the patient P so as to allow the self-solution of technical or medical problems. In addition, the audio alarms may be increased in volume and any manual overrides may be disabled.

The above system 10 may also be used to broadcast or transfer information or commands or alarms between cylinder systems 14 or to cylinder systems 14. For example, as each cylinder system 14 includes an alarm and each cylinder system 14 is connected to the system 10, the system may be used to cause an evacuation alarm to be transmitted to each cylinder system 14 so as to allow staff to respond accordingly. In addition, instructions may be sent to a home patient at location F. It will be appreciated that any form of data or commands may be transmitted to or from cylinder systems 14 at any one or more of locations A to F and that modifications, deletion and variations to the data being transferred, alarms being created or modified and controls being implemented is possible. The above specific examples are, therefore, illustrative only.

It will be understood that when the second monitoring system is not within range of a Wi-Fi network, for example during transportation in a truck or ambulance, data can be transmitted to the further device, cloud based server or remote computer via a mobile network.

The first monitoring system can also be provided with a motion detector (not shown) to detect movement of the gas cylinder, specifically, that the gas cylinder is changing location. If movement is detected then the software can be configured to immediately broadcast data to the second monitoring system to identify the location of the gas cylinder and its status.

The second monitoring system may send additional data such as command signals to the first monitoring system 16 for causing control over the operation of the cylinder system 14 such as to prevent inadvertent gas delivery whilst within the filling station and/or to automatically close and maintain closed the valve 34 during an adverse event such as a fire or excessive vibration caused by, for example, an earthquake. These control parameters may be applied in any one of the locations A to F detailed in the above and below descriptions. Cylinder specific data and/or environment specific data is broadcast to the second monitoring system for further transmission within the overall system 10. Information such as filling date may be used to calculate an expiry date so as to ensure good management of gas safety. Environment specific data may be used to control the cylinder valve and/or alarms in the event of an adverse environmental event such as detection of smoke, unexpected temperature variation, adverse vibration etc.

In an alternative embodiment, the processing of data to determine the time and/or time interval at which advertisement package (AP) is broadcast can be determined by a processor in the second monitoring system or in the computer system 20 as opposed to internally in the first monitoring system 16. If the processor is in the second monitoring system then the advertisement package is received from the first processing system via Bluetooth transmission. If the processor is in the computer system 20 then the computer system 20 receives the advertisement package (AP) via the broadcast from the first monitoring system 16 using Bluetooth transmission, and from the hub station 18a-f over a Wi-Fi network. The calculated time and/or time interval for broadcasting the advertisement package (AP) from the first monitoring system 16 is transmitted from the hub station 18*a-f* to the first monitoring system directly via Bluetooth transmission, or from the computer system over a Wi-Fi network and from the hub station 18*a-f* to the first monitoring system 16 using Bluetooth transmission. It will be appreciated that the first monitoring system 16 and the hub station 18*a-f* must be sufficiently close to each other to enable transmission of data using Bluetooth which has a shorter range compared to Wi-Fi transmission. The distance between the computer system and the hub station is less restricted by virtue of the longer distances over which data can be transmitted using Wi-Fi. The time and location which the advertisement package (AP) is broadcast can also be determined within the computer system 20 or with any further device in communication with the first monitoring system 16 either directly or via the second monitoring system 18.

It will be appreciated that when the system is operating in the first mode, the first 16 and second 18 monitoring systems do not become connected or paired. The system can also operate in a second mode where the first and second monitoring systems connect or pair to enable transfer of data therebetween. Transfer of certain types of data is more appropriate when a connection between the two monitoring systems is made compared to sending data without connecting or pairing. Examples of data include sending instructions to the first monitoring system to control gas cylinder operation or alarm states, or reconfiguring the advertisement packages, although such data can also be transmitted to the first monitoring system without connecting.

In the above embodiments, data is broadcast from the first monitoring device by way of an advertisement package, albeit at varying time intervals. The first monitoring device can therefore be considered as acting like a beacon broadcasting data which is then received by the second monitoring device when in range using Bluetooth transmissions. The data content of the advertisement package also varies depending on the status of the system, by which is meant the cylinder, patient and environment, and therefore the package is dynamic in nature. The second monitoring system can also transmit data and/or instructions to the first monitoring system using Bluetooth, or other wireless communication if the first monitoring system is suitably enabled. The use of Bluetooth to send data has the advantage that firstly less energy is consumed for any given broadcast, and secondly that by reducing the number of broadcasts according to the monitored data and location associated with the first monitoring system, less energy is consumed compared to known continuous Bluetooth transmissions which require pairing and therefore a constant connection. The reduced energy requirement of the first monitoring system during broadcast or reception of data is clearly important in a battery-powered system. The transmission and reception of data and information from the second monitoring system to a further device, cloud or computer system relies on Wi-Fi which is necessary to transmit over greater distances, but more energy consuming. However, the energy consumption is less of a concern as the second monitoring system is connected to mains power in contrast to the first monitoring system.

What we claim is:

1. A gas cylinder monitoring system comprising:
   a gas cylinder for receiving and distributing gas contained therein,
   a first monitoring system associated with the gas cylinder operable to monitor data associated with the gas cylinder and having a transmitter operable to broadcast the data at a controlled time and/or time interval in a discrete advertisement package, and
   a second monitoring system associated with one or more locations in which the first monitoring system may reside and having a receiver operable in a first mode to receive the advertisement package broadcast from the first monitoring system when the second monitoring system is within range of the first monitoring system,
   wherein the first monitoring system and the second monitoring system are operable to transfer additional data therebetween, and the additional data includes data to configure the advertisement package and/or the additional data includes data to vary the time and/or time interval at which the advertisement package is broadcast from the first monitoring system.

2. The system according to claim 1, in which the advertisement package includes fixed data which does not vary with the operation of the gas cylinder and variable data.

3. The system according to claim 2, in which the controlled time and/or time interval is dependent on the variable data.

4. The system according to claim 1, further comprising a processor operable to identify the second monitoring system receiving data from the first monitoring system to determine the location of the first monitoring system.

5. The system according to claim 4, in which the controlled time and/or time interval is dependent on the location of the first monitoring system.

6. The system according to claim 4, in which the second monitoring system is a plurality of hub stations at known locations, and wherein the processor is operable to identify one or more of the plurality of hub stations receiving data from the first monitoring system to determine the location of the first monitoring system.

7. The system according to claim 6, in which the processor is operable to identify the hub station receiving data at the highest signal strength to determine the location of the first monitoring system.

8. The system according to claim 6, in which the processor is operable to triangulate between hub stations within range of the first monitoring system to determine the location of the first monitoring system.

9. The system according to claim 1, in which the receiver is further operable in a second mode to connect the second monitoring system to the first monitoring system.

10. The system according to claim 9, in which the first and second monitoring systems are operable to connect with each other to transfer the additional data therebetween.

11. The system according to claim 1, in which the additional data includes data to configure the advertisement package.

12. The system according to claim 1, in which the additional data includes data to vary the time and/or time interval at which the advertisement package is broadcast from the first monitoring system.

13. The system according to claim 1, in which the additional data includes data to control an output of the gas cylinder.

14. The system according to claim 13, in which the output is one or more of enabling an alarm, disabling an alarm, or controlling gas flow.

15. The system according to claim 1, in which the first monitoring system is further operable to broadcast the advertisement package at a time and/or a time interval that is dependent on the location of the first monitoring system.

16. The system according to claim 1, in which the transmitter is a Bluetooth transmitter.

17. The system according to claim 1, in which the advertisement package is broadcast in less than 50 milliseconds.

18. The system according to claim 1, in which the data is selected from the group consisting of one or more of cylinder location, cylinder identification number, cylinder size, cylinder pressure, cylinder operating mode, battery life, tamper state, firmware version, gas supply time remaining, expiry date, cylinder type, environmental temperature, gas usage, time since filling, rate of gas usage, internal cylinder gas pressure, internal cylinder gas temperature, usage data, transportation data, and gas remaining.

19. The system according to claim 18, in which the first monitoring system is operable to decrease the time interval as the gas supply time remaining decreases.

20. The system according to claim 18, in which the first monitoring system is operable to immediately broadcast the data when the gas supply time reaches a pre-determined lower threshold.

21. The system according to claim 1, in which the data from the first monitoring system identifies an operational mode of the gas cylinder.

22. The system according to claim 21, in which the time and/or time interval is determined by the operational mode.

23. The system according to claim 21, in which the operational mode of the gas cylinder is selected from the group consisting of one or more of a deep sleep mode, a connected mode, a standby mode, a gas delivery mode, or a fault mode.

24. The system according to claim 23, in which the first monitoring system is operable to immediately broadcast the data if the gas cylinder enters a fault mode or a gas delivery mode or a connected mode.

25. The system according to claim 23, in which the time interval is less than 2 minutes when the gas cylinder is in gas delivery mode.

26. The system according to claim 6, in which the known locations are selected from the group consisting of one or more of a filling station, a storage station, a hospital ward, a patient's home, an ambulance, an operating theatre and a transportation vehicle.

27. The system according to claim 26, in which the time interval between broadcasts of the data is greater than 30 minutes when the gas cylinder is in a storage station.

28. The system according to claim 26, in which the first monitoring system is operable to broadcast the data when the gas cylinder arrives in the filling station.

29. The system according to claim 26, in which the first monitoring system is operable to broadcast the data when the gas cylinder leaves the filling station.

30. The system according to claim 1, further comprising a motion sensor operable to detect movement of the first monitoring system, in which the first monitoring system is operable to broadcast the data immediately if movement is detected.

31. The system according to claim 1, further comprising a computer system in communication with the second monitoring system operable to receive information therefrom relating to the data associated with the gas cylinder and/or the location of the second monitoring system.

* * * * *